US009498342B2

(12) United States Patent
Wright et al.

(10) Patent No.: US 9,498,342 B2
(45) Date of Patent: Nov. 22, 2016

(54) KNEE PROSTHESIS HAVING COMMONLY-SIZED PATELLA COMPONENTS WITH VARYING THICKNESSES AND PEAK SURFACE DIAMETERS

(75) Inventors: Abraham P. Wright, Winona Lake, IN (US); David S. Barrett, Southhampton (GB); William P. Barrett, Seattle, WA (US)

(73) Assignee: DEPUY IRELAND UNLIMITED COMPANY (IE)

(*) Notice: Subject to any disclaimer, the term of this patent is extended or adjusted under 35 U.S.C. 154(b) by 1008 days.

(21) Appl. No.: 12/981,953

(22) Filed: Dec. 30, 2010

(65) Prior Publication Data

US 2012/0172993 A1 Jul. 5, 2012

(51) Int. Cl.
*A61F 2/38* (2006.01)
*A61F 2/30* (2006.01)

(52) U.S. Cl.
CPC .... *A61F 2/3877* (2013.01); *A61F 2002/30616* (2013.01)

(58) Field of Classification Search
CPC ........................................................ A61F 2/38
USPC .................... 623/20.18–20.21, 21.11–21.17
See application file for complete search history.

(56) References Cited

U.S. PATENT DOCUMENTS

| | | | |
|---|---|---|---|
| 4,151,615 A | 5/1979 | Hall | |
| 5,580,353 A * | 12/1996 | Mendes et al. | 623/20.18 |
| 2003/0088315 A1 * | 5/2003 | Supinski | 623/20.2 |
| 2004/0143336 A1 | 7/2004 | Burkinshaw | |
| 2004/0143338 A1 | 7/2004 | Burkinshaw et al. | |
| 2007/0265708 A1 | 11/2007 | Brown et al. | |
| 2008/0188942 A1 | 8/2008 | Brown et al. | |
| 2009/0326661 A1 | 12/2009 | Wright et al. | |

FOREIGN PATENT DOCUMENTS

| | | |
|---|---|---|
| CN | 2681706 Y | 3/2005 |
| CN | 1903145 A2 | 1/2007 |
| CN | 101160107 A | 4/2008 |
| CN | 101330883 B1 | 12/2008 |
| CN | 101617968 A1 | 1/2010 |
| CN | 101879099 A | 11/2010 |
| EP | 2140836 A1 | 1/2010 |
| GB | 2301032 A | 11/1996 |
| WO | 2007070859 A2 | 6/2007 |

OTHER PUBLICATIONS

Benjamin C. Bengs, MD and Richard D. Scott, MD, The Effect of Patellar Thickness on Intraoperative Knee Flexion and Patellar Tracking in Total Knee Arthroplasty, The Journal of Arthroplasty, 2006, 6 pages, vol. 21 No. 5.
European Search Report, European Application No. 11194972.3-2310, Mar. 20, 2012, 7 pages.
English translation of Chinese Search Report for Chinese Application No. 201110462726.3, Dec. 30, 2011, 3 pages.

* cited by examiner

*Primary Examiner* — Yashita Sharma
(74) *Attorney, Agent, or Firm* — Barnes & Thornburg LLP

(57) ABSTRACT

An orthopaedic implant assembly includes a plurality of commonly-sized dome patella components. Each of the commonly-sized dome patella components may be provided in various thicknesses and/or peak surface diameters.

4 Claims, 7 Drawing Sheets

KNEE PROSTHESIS HAVING COMMONLY-SIZED PATELLA COMPONENTS WITH VARYING THICKNESSES AND PEAK SURFACE DIAMETERS

TECHNICAL FIELD

The present disclosure relates generally to an implantable orthopaedic prosthesis, and more particularly to an implantable orthopaedic prosthesis having commonly-sized dome patella components with varying thicknesses and peak surface diameters.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a patella replacement procedure, a orthopaedic prosthesis is implanted into the patient's patella. Specifically, a prosthetic patella component is secured to the patient's natural patella such that its posterior surface articulates with a femoral component during extension and flexion of the knee.

A conventional dome patella component is embodied as a dome-shaped polymer bearing having a spherical dome profile. As such, changing the thickness of the component requires a change in the size of the component (i.e., the component's outer diameter). In other words, the thickness and size of the component are geometrically dependent on one another. For example, the minimum thickness of certain prior art 41 mm dome patella components is ~11.4 mm. This may be too thick for a given surgical application. However, a reduction in thickness would also require a reduction in component size (i.e., the component's outer diameter). Such dimensional dependency can create challenges in regard to the surgical correction of patellafemoral gap imbalances.

SUMMARY

According to one aspect, an implantable orthopaedic knee prosthesis assembly includes a first dome patella component that has a posterior bearing surface configured to articulate with the femoral condyles of an implantable femoral component, and an anterior surface having a number of pegs extending outwardly therefrom. When viewed in a coronal cross sectional view, the posterior bearing surface of the first dome patella component has a curved peak surface that includes a posterior-most point of the first dome patella component. A first imaginary line segment extends orthogonally from the anterior surface of the first dome patella component to the posterior-most point of the first dome patella component. The implantable orthopaedic knee prosthesis assembly also includes a second dome patella component that has a posterior bearing surface configured to articulate with the femoral condyles of an implantable femoral component and an anterior surface having a number of pegs extending outwardly therefrom. The medial/lateral width of the second dome patella component is the same as the medial/lateral width of the first dome patella component. When viewed in a coronal cross sectional view, the posterior bearing surface of the second dome patella component has a curved peak surface that includes a posterior-most point of the second dome patella component. A second imaginary line segment extends orthogonally from the anterior surface of the second dome patella component to the posterior-most point of the second dome patella component. The second imaginary line segment being longer than the first imaginary line segment.

The implantable orthopaedic knee prosthesis assembly also includes a third dome patella component that has a posterior bearing surface configured to articulate with the femoral condyles of an implantable femoral component and an anterior surface having a number of pegs extending outwardly therefrom. The medial/lateral width of the third dome patella component is the same as the medial/lateral width of both the first dome patella component and the second dome patella component. When viewed in a coronal cross sectional view, the posterior bearing surface of the third dome patella component has a curved peak surface that includes a posterior-most point of the third dome patella component. A third imaginary line segment extends orthogonally from the anterior surface of the third dome patella component to the posterior-most point of the third dome patella component. The third imaginary line segment being longer than both the first imaginary line segment and the second imaginary line segment.

The curved peak surface of both the first and second dome patella components may include a partial hemispherically-shaped surface. The posterior bearing surface of both the first and second dome patella components may further include a conically-shaped surface that extends anteriorly away from the partial hemispherically-shaped surface and transitions into a rounded edge surface that extends anteriorly away from the conically-shaped surface in the direction toward the anterior surface.

Each of the first and second dome patella components may include a monolithic polyethylene body.

The first and second dome patella components include a first number of pegs extending anteriorly away from the anterior surface of the first dome patella component. The first number of pegs have the same diameter as the second number of pegs. The first number of pegs are arranged in the same pattern on the anterior surface of the first dome patella component as the second number of pegs are arranged on the anterior surface of the second dome patella component.

According to another aspect, an implantable orthopaedic knee prosthesis assembly includes a femoral component having a medial condyle surface and a lateral condyle surface and a plurality of dome patella components configured to be separately positioned in contact with the condyle surfaces of the femoral component. Each of the plurality of dome patella components has a medial/lateral width that is the same as each of the other of the plurality of dome patella components. Each of the plurality of dome patella components also includes a posterior bearing surface having a medial articular surface configured to articulate with the medial condyle surface of the femoral component and a lateral articular surface configured to articulate with the lateral condyle surface of the femoral component. Each of the plurality of dome patella components has an anterior/posterior thickness that is different from at least some of the other of the plurality of dome patella components.

Each of the plurality of dome patella components includes an anterior surface having a number of pegs extending outwardly therefrom. The posterior bearing surface of each of the plurality of dome patella components has a curved peak surface that includes a posterior-most point of the dome patella component. The anterior/posterior thickness of each of the plurality of dome patella components may be defined by an imaginary line segment that extends orthogonally from the anterior surface to the posterior-most point.

The posterior bearing surface of each of the plurality of dome patella components may include a partial hemispherically-shaped peak surface and a conically-shaped surface that extends anteriorly away from the partial hemispherically-shaped peak surface. The conically-shaped surface transitions into a rounded edge surface that extends anteriorly away from the conically-shaped surface.

Each of the plurality of dome patella components may be embodied as a monolithic polyethylene body.

Each of the plurality of dome patella components includes an anterior surface having a number of pegs extending outwardly therefrom. The corresponding pegs of each of the plurality of dome patella components have the same diameter as one another. The pegs of each of the plurality of dome patella components may be arranged in the same pattern as one another.

According to another aspect, an implantable orthopaedic knee prosthesis assembly includes a first dome patella component that has a posterior bearing surface configured to articulate with the femoral condyles of an implantable femoral component, and an anterior surface having a number of pegs extending outwardly therefrom. The posterior bearing surface of the first dome patella component has a partial hemispherically-shaped peak surface that includes a posterior-most point of the first dome patella component and a conically-shaped surface that extends anteriorly away from the partial hemispherically-shaped surface.

The implantable orthopaedic knee prosthesis assembly also includes a second dome patella component that has a posterior bearing surface configured to articulate with the femoral condyles of an implantable femoral component and an anterior surface having a number of pegs extending outwardly therefrom. The medial/lateral width if the second dome patella component is the same as the medial/lateral width of the first dome patella component. The posterior bearing surface of the second dome patella component has a partial hemispherically-shaped peak surface that includes a posterior-most point of the second dome patella component and a conically-shaped surface that extends anteriorly away from the partial hemispherically-shaped peak surface. The diameter of the partial hemispherically-shaped peak surface of the second dome patella component is greater than the diameter of the partial hemispherically-shaped peak surface of the first dome patella component.

The implantable orthopaedic knee prosthesis assembly may further include a third dome patella component that has a posterior bearing surface configured to articulate with the femoral condyles of an implantable femoral component and an anterior surface having a number of pegs extending outwardly therefrom. The medial/lateral width of the third dome patella component is the same as the medial/lateral width of both the first dome patella component and the second dome patella component. The posterior bearing surface of the third dome patella component has a partial hemispherically-shaped peak surface that includes a posterior-most point of the third dome patella component and a conically-shaped surface that extends anteriorly away from the partial hemispherically-shaped peak surface. The diameter of the partial hemispherically-shaped peak surface of the third dome patella component is greater than the diameters of the partial hemispherically-shaped peak surfaces of both the first and second dome patella components.

The conically-shaped surface of both the first and second dome patella components transitions into a rounded edge surface that extends anteriorly away from the conically-shaped surface in the direction toward the anterior surface.

Each of the first and second dome patella components may be embodied as a monolithic polyethylene body.

The first dome patella component may include a first number of pegs extending anteriorly away from the anterior surface of the first dome patella component, with the second dome patella component including a second number of pegs extending anteriorly away from the anterior surface of the second dome patella component. The first number of pegs have the same diameter as the second number of pegs. The first number of pegs are arranged in the same pattern on the anterior surface of the first dome patella component as the second number of pegs are arranged on the anterior surface of the second dome patella component.

According to another aspect, an implantable orthopaedic knee prosthesis assembly includes a femoral component having a medial condyle surface and a lateral condyle surface and a plurality of dome patella components configured to be separately positioned in contact with the condyle surfaces of the femoral component. Each of the plurality of dome patella components has a medial/lateral width that is the same as each of the other of the plurality of dome patella components. Each of the plurality of dome patella components has a conically-shaped surface configured to articulate with the lateral condyle surface of the femoral component, and a partial hemispherically-shaped peak surface having a diameter that is different from the diameter of the hemispherically-shaped peak surfaces of at least some of the other of the plurality of dome patella components.

The partial hemispherically-shaped peak surface of each of the plurality of dome patella components includes a posterior-most point of the dome patella component, and extends anteriorly and transitions to the conically-shaped surface of the dome patella component.

Each of the plurality of dome patella components includes an anterior surface having a number of pegs extending outwardly therefrom.

Each of the patella components may be embodied as a monolithic polyethylene body.

Each of the plurality of dome patella components includes an anterior surface having a number of pegs extending outwardly therefrom. The corresponding pegs of each of the plurality of dome patella components have the same diameter as one another. The pegs of each of the plurality of dome patella components are arranged in the same pattern as one another.

BRIEF DESCRIPTION OF THE DRAWINGS

The detailed description particularly refers to the following figures, in which.

DETAILED DESCRIPTION OF THE DRAWINGS

Figure 1:
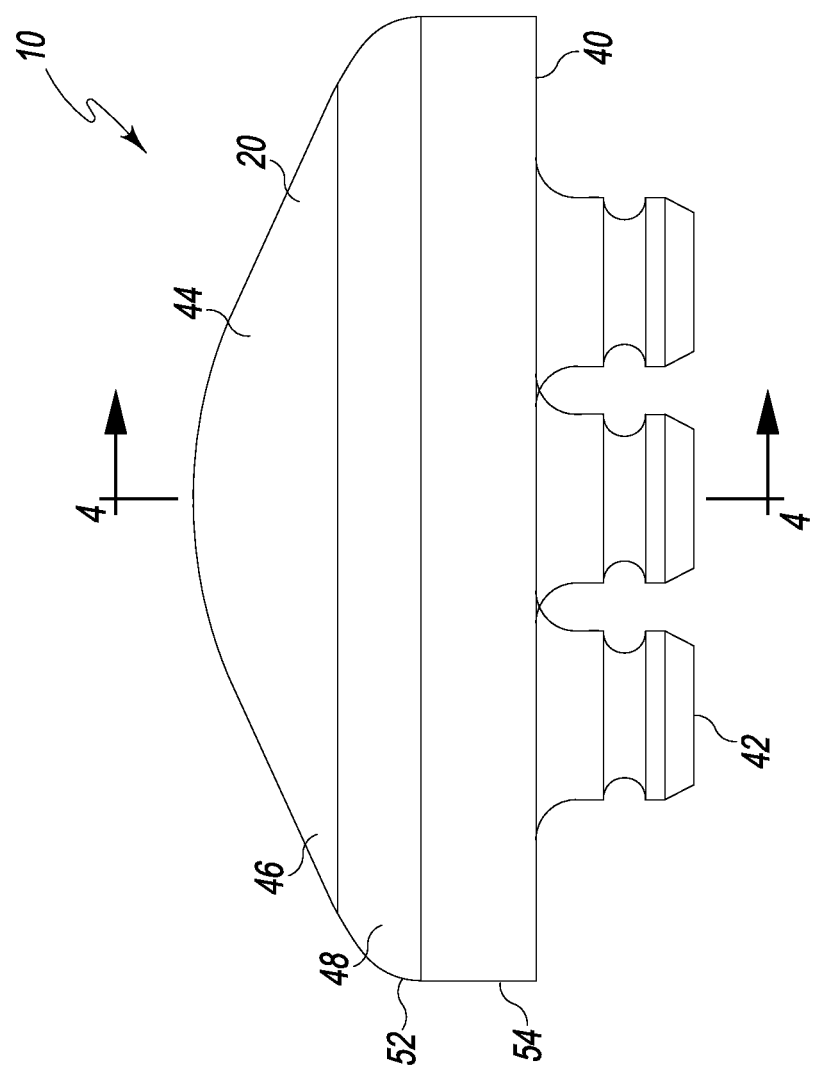
FIG. 1 is an elevation view of a dome patella component of a knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 2:
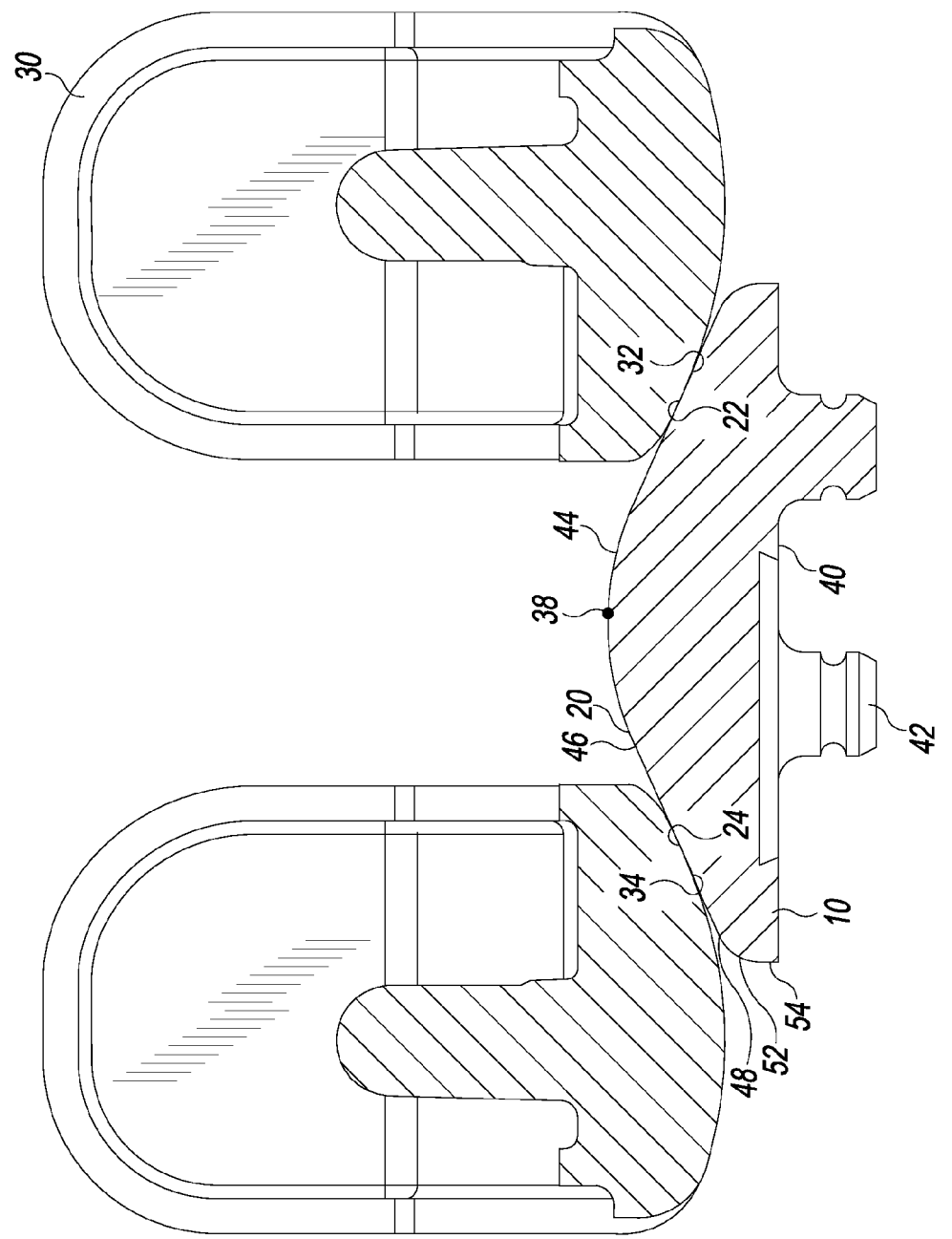
FIG. 2 is a coronal cross sectional view showing the dome patella component of FIG. 1 positioned in articular contact with a femoral component of the knee prosthesis.

Referring now to FIGS. 1-4, there is shown a dome patella component 10 of an implantable knee prosthesis. As will be described below in greater detail, a number of commonly-sized dome patella components 10 (i.e., each of them having the same diameter) may be provided in different thicknesses. As shown in FIG. 2, the knee prosthesis also includes a femoral component 30 that is configured to be secured to a surgically-prepared end of a patient's distal femur (not shown). The dome patella component 10 includes a posterior bearing surface 20 configured to articulate with the condylar surfaces of the femoral component 30. In particular, the posterior bearing surface 20 of the dome patella component 10 includes a lateral articular surface 22 and a medial articular surface 24. The articular surfaces 22, 24 are configured to articulate with a lateral condyle surface 32 and a medial condyle surface 34, respectively, of the femoral component 30. Specifically, the femoral component 30 is configured to emulate the configuration of the patient's natural femoral condyles, and, as such, the lateral condyle surface 32 and the medial condyle surface 34 are configured (e.g., curved) in a manner which mimics the condyles of the natural femur. The lateral condyle surface 32 and the medial condyle surface 34 are spaced apart from one another thereby defining an intercondylar notch therebetween.

As can be seen in FIG. 1, the dome patella component 10 also includes a flat anterior surface 40 having a number of fixation members, such as pegs 42, extending away therefrom. The pegs 42 are configured to be implanted into a surgically prepared posterior surface of the patient's natural patella (not shown). In such a way, the posterior bearing surface 20 of the dome patella component 10 faces toward the femoral component 30 thereby allowing the posterior bearing surface 20 to articulate with the femoral condyle surfaces 32, 34 during flexion and extension of the patient's knee.

The dome patella component 10 is embodied as a monolithic polymer body constructed with a material that allows for smooth articulation between the dome patella component 10 and the femoral component 30. One such polymeric material is polyethylene such as ultrahigh molecular weight polyethylene (UHMWPE). The femoral component 30 may be constructed with a biocompatible metal, such as a cobalt chrome alloy, although other materials, such as ceramics, may also be used.

Figure 3:
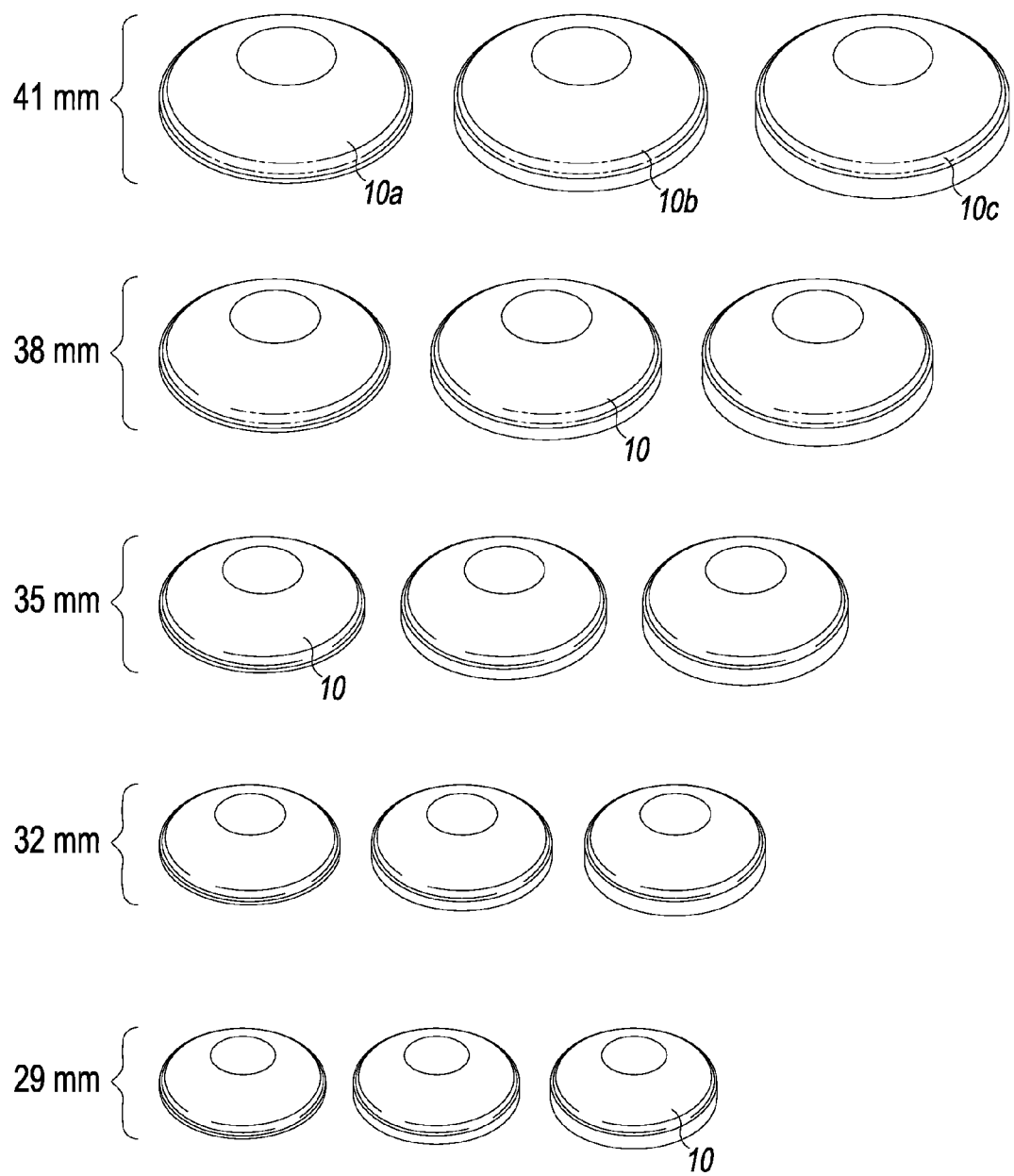
FIG. 3 is a chart showing the dome patella component of FIG. 1 provided in a number of different component width and thickness options.

As will be discussed in greater detail, the geometric design of the dome patella component 10 removes the dependency between component size (i.e., component outer diameter) and component thickness. In particular, as shown in the chart of FIG. 3, a number of commonly-sized dome patella components 10 (i.e., components having the same diameter) can be fabricated across a range of thicknesses. Having various component thicknesses available at each component size facilitates the surgeon's efforts in patellofemoral balancing. For example, if the patient's patella is loose in both the extension and flexion gaps, the surgeon can select a thicker patella of the same size to ensure proper bone coverage (or vice versa if the patient's patella is tight in the extension and flexion gaps). This is in contrast with prior art designs in which the dimensional dependency would require a change in component size (i.e., component outer diameter) to increase or decrease the thickness of the component.

Figure 4:
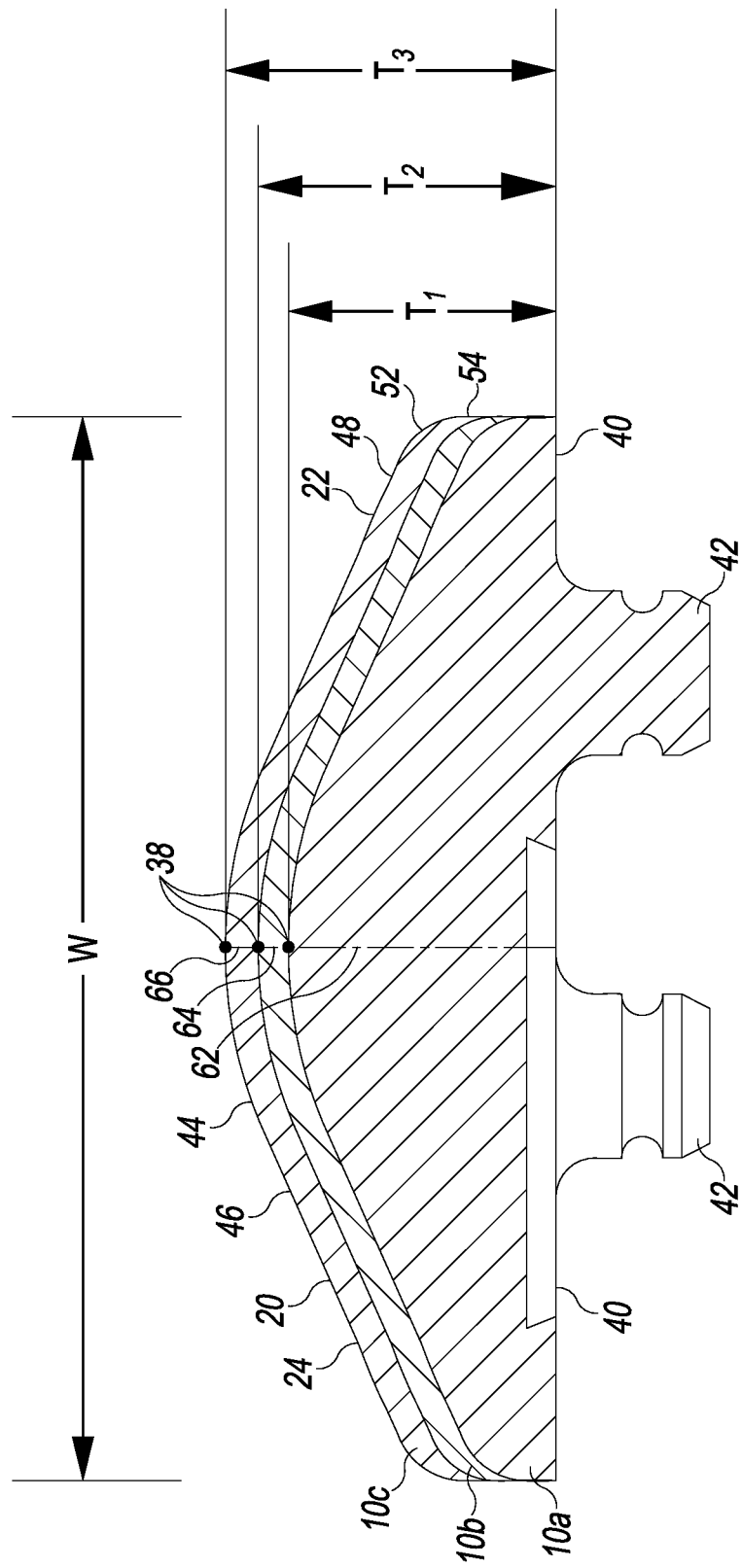
FIG. 4 is a coronal cross sectional view showing a number of commonly-sized dome patella components with differing thicknesses superimposed upon one another.

Referring now to FIGS. 1 and 4, the geometry of the posterior bearing surface 20 of the dome patella component 10 is shown in greater detail. The posterior bearing surface 20 of the dome patella component 10 has a curved peak surface 44. The curved peak surface 44 defines the posterior-most surface of the dome patella component 10. Specifically, a point on the curved peak surface 44 defines the posterior-most point 38 of the dome patella component 10. The curved peak surface 44 is embodied as a partial hemispherically-shaped surface, i.e., a surface that is a section of a sphere that is less than a hemisphere. The partial hemispherically-shaped peak surface 44 is geometrically decoupled from the remainder of the posterior bearing surface 20. In particular, the partial hemispherically-shaped peak surface 44 does not extend across the entire posterior bearing surface, but rather it extends anteriorly away from the posterior-most point 38 in the general direction toward the anterior surface 40 and transitions to a substantially conically-shaped surface 46. The conically-shaped surface 46 in turn transitions to a rounded edge surface 48 that extends anteriorly away from the conically-shaped surface 46 in the direction toward the anterior surface 40 of the dome patella component 10. In the illustrative embodiment of the dome patella component 10 described herein, the rounded edge surface 48 includes a curved corner surface 52 that transitions from the to the conically-shaped surface 46 and a flat surface 54 that transitions the curved corner surface 52 to the anterior surface 40 of the dome patella component 10.

In the illustrative embodiment described herein, the geometric design of the posterior bearing surface 20 in which the partial hemispherically-shaped peak surface 44 transitions to the conically-shaped surface 46 removes the dependency between component size (i.e., component outer diameter) and component thickness. As such, the dome patella components 10 may be provided in a range of component sizes. For example, as shown in the chart of FIG. 3, the dome patella components 10 may be provided in 41 mm, 38 mm, 35 mm, 32 mm, and 29 mm sizes. In a conventional nomenclature, such sizes represent the diameter of the component (e.g., a size 41 mm patella component has a 41 mm outer diameter). By eliminating the dimensional dependency of prior art designs, the patella components 10 of each of the various sizes may be provided in a number of various thicknesses. For example, the 41 mm patella component 10 may be provided in three thicknesses such as 10.5 mm, 11.0 mm, and 11.5 mm. It should be appreciated that such thicknesses are illustrative in nature. The example noted above is in contrast to prior art designs in which, for example, the thinnest 41 mm component has a thickness of approximately 11.4 mm due to the dimensional dependency of the design. It should be appreciated that although each size of dome patella component 10 is shown in the chart of FIG. 3 as having three different thickness options, such options are illustrative in nature. For example, each size of component may have fewer or more different thickness options available. Moreover, although the thickness of the components 10 within a common size are varied in 5 mm increments in the example noted above, the magnitude of such increments may be varied to fit the needs of a given design.

The different component thickness options is demonstrated geometrically in the coronal cross sectional view of FIG. 4 where three commonly-sized dome patella components 10a, 10b, 10c are superimposed upon one another. In the illustrative example of FIG. 4, a 41 mm dome patella component 10 (i.e., W=41 mm) is shown in three different thicknesses such as 10.5 mm (i.e., $T_1$=10.5 mm), 11.0 mm (i.e., $T_2$=11.0 mm), and 11.5 mm (i.e., $T_3$=11.5 mm). As can be seen in FIG. 4, each of the dome patella components 10a, 10b, 10c has the same medial/lateral width (W) as one another (i.e., in the case of the illustrative example, W=41 mm). As can also be seen in FIG. 4, each of the dome patella components 10a, 10b, 10c has an imaginary line segment extending through it in the anterior/posterior direction. The length of the respective imaginary line segments defines the thickness of the respective patella components 10a, 10b, 10c. Specifically, an imaginary line segment 62 extends orthogonally from the anterior surface 40 of the patella component 10a through the posterior-most point 38 of the patella component 10a, an imaginary line segment 64 extends orthogonally from the anterior surface 40 of the patella component 10b through the posterior-most point 38 of the patella component 10b, and an imaginary line segment 66 extends orthogonally from the anterior surface 40 of the patella component 10c through the posterior-most point 38 of the patella component 10c. The line segment 66 (i.e., in the case of the illustrative example, $T_3$=11.5 mm) is longer than the line segment 64 (i.e., in the case of the illustrative example, $T_2$=11.0 mm), which is in turn longer than the line segment 62 (i.e., in the case of the illustrative example, $T_1$=10.5 mm).

Figure 5:
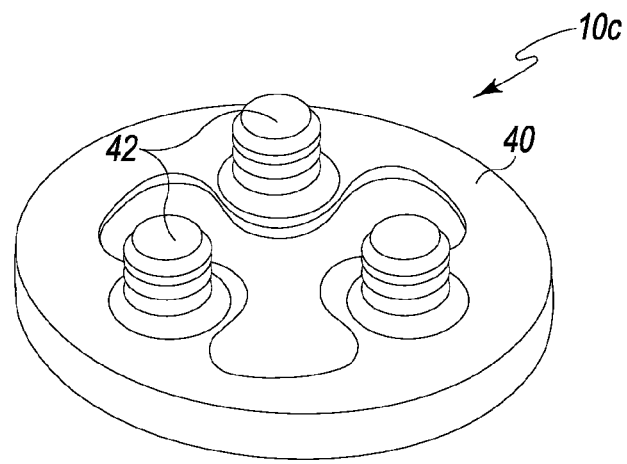
FIGS. 5-7 are bottom perspective views of the dome patella components of FIG. 4.
Figure 6:
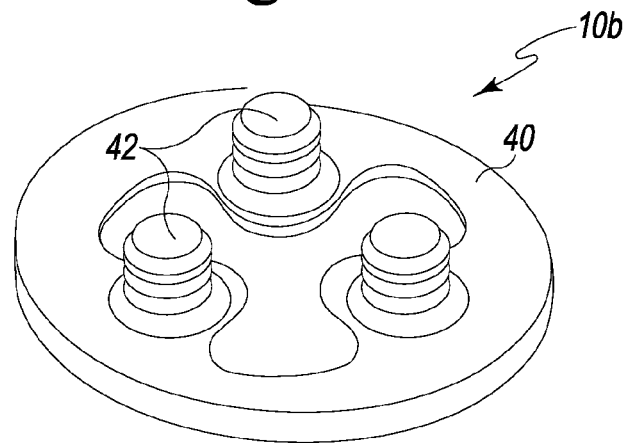
Figure 7:
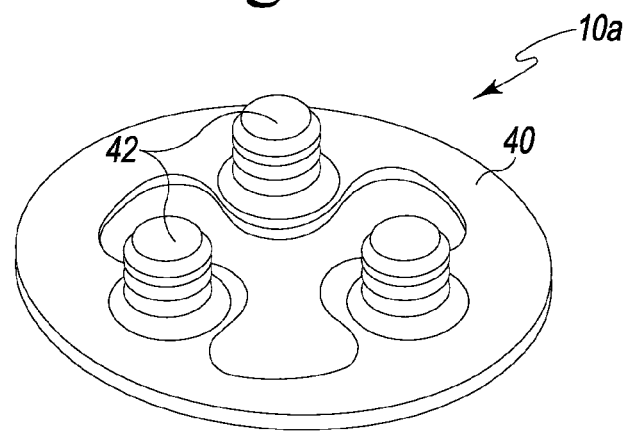

As shown in FIGS. 5-7, the various dome patella components 10 of a given component size have the same fixation features. In particular, even though the dome patella components of a given component size have various thicknesses, the pegs 42 of the components 10 have the same diameter and are arranged in the same pattern (i.e., arranged at the same location) as one another. For example, a 41 mm dome patella component 10 is shown in FIGS. 5-7 in three different thicknesses (e.g., 11.5 mm in FIG. 5, 11.0 mm in FIG. 6, and 10.5 mm in FIG. 7). As can be seen in such an example, even though the 41 mm dome patella components have different thicknesses, the pegs 42 of the components 10 have the same diameter and are arranged in the same pattern (i.e., arranged at the same location) as one another. As such, a common set of instruments and a common surgical technique may be used for bone preparation and device implantation.

Figure 8:
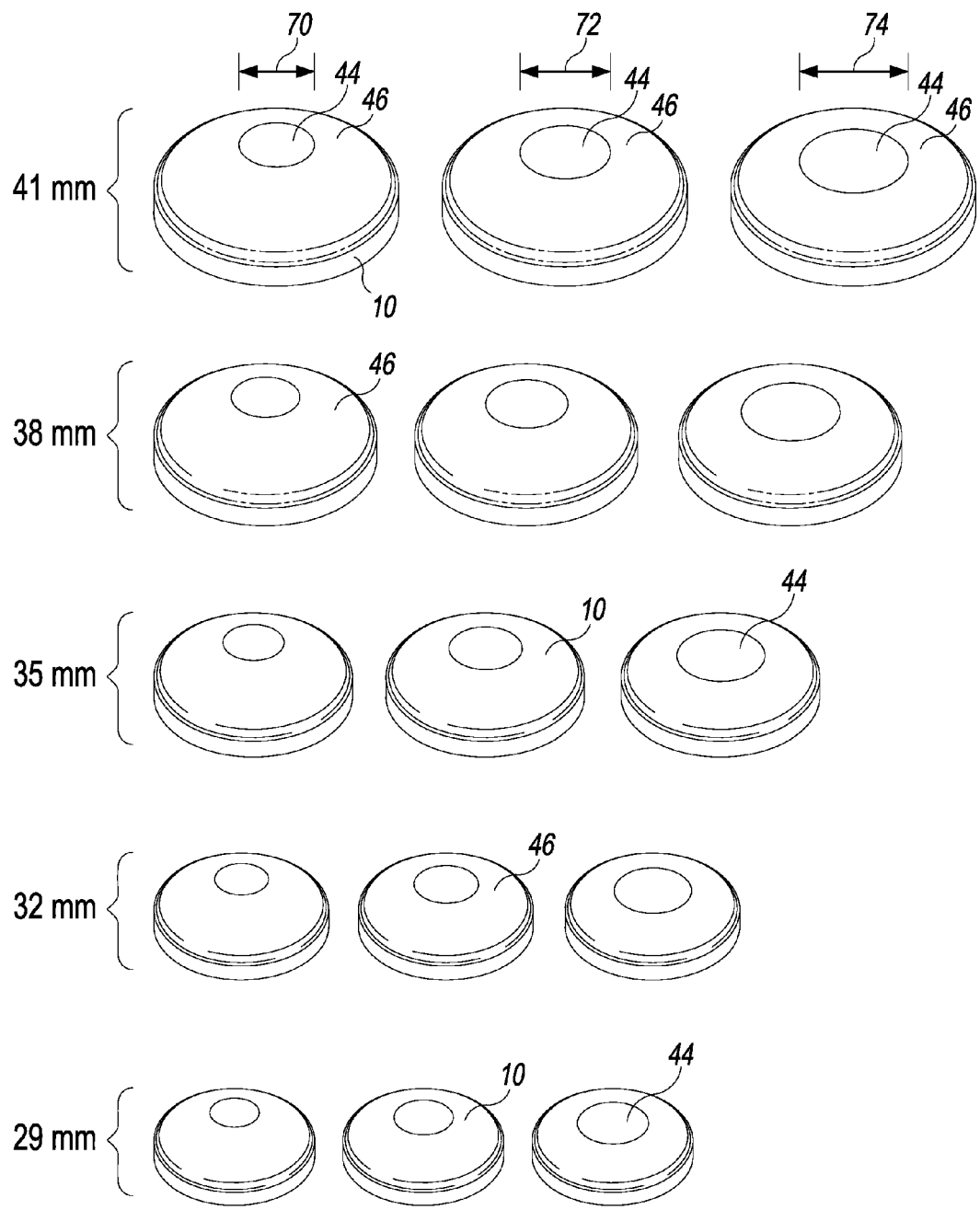
FIG. 8 is a chart similar to FIG. 3, but showing the dome patella component of FIG. 1 provided in a number of different component width and peak diameter options.

In lieu of, or in addition to, providing the dome patella component 10 in various thicknesses, the geometric design of the posterior bearing surface 20 allows for the dome patella component 10 to be provided in various peak diameter options. In particular, since the partial hemispherically-shaped peak surface 44 is geometrically decoupled from the remainder of the posterior bearing surface 20, the diameter of the partial hemispherically-shaped peak surface 44 may be varied within dome patella components 10 of the same size (i.e., components having the same outer diameter). In particular, by eliminating the dimensional dependency of prior art designs, the patella components 10 of each of the various sizes may be provided in a number of various peak diameters. For example, as shown in the chart of FIG. 8, each of the commonly-sized patella components 10 may be provided in three different peak surface diameters. For example, the 41 mm patella component 10 may be embodied in three different peak surface diameters 70, 72, 74. Likewise, the 35 mm patella component 10 (or any of the other component sizes) may be provided in a number of different peak surface diameters. It should be appreciated that although each size of dome patella component 10 is shown in the chart of FIG. 8 as having three different peak surface diameter options, such options are illustrative in nature. For example, each size of component may have fewer or more different peak diameter options available.

It should be appreciated that altering the diameter of the partial hemispherically-shaped-peak surface 44 changes the morphology of the dome patella component 10. In particular, by increasing the diameter of the partial hemispherically-shaped peak surface 44, the component 10 becomes flatter. By decreasing the diameter of the partial hemispherically-shaped peak surface 44, the component 10 becomes more pointed. This is useful during patellafemoral balancing in cases where the extension gap does not equal the flexion gap. By modifying the diameter of the partial hemispherically-shaped peak surface 44, the extension gap can be tightened or loosened while the flexion gap remains unchanged. By doing so, the surgeon may choose a patella option that creates the desired tension in the flexion and extension gaps.

Figure 9:
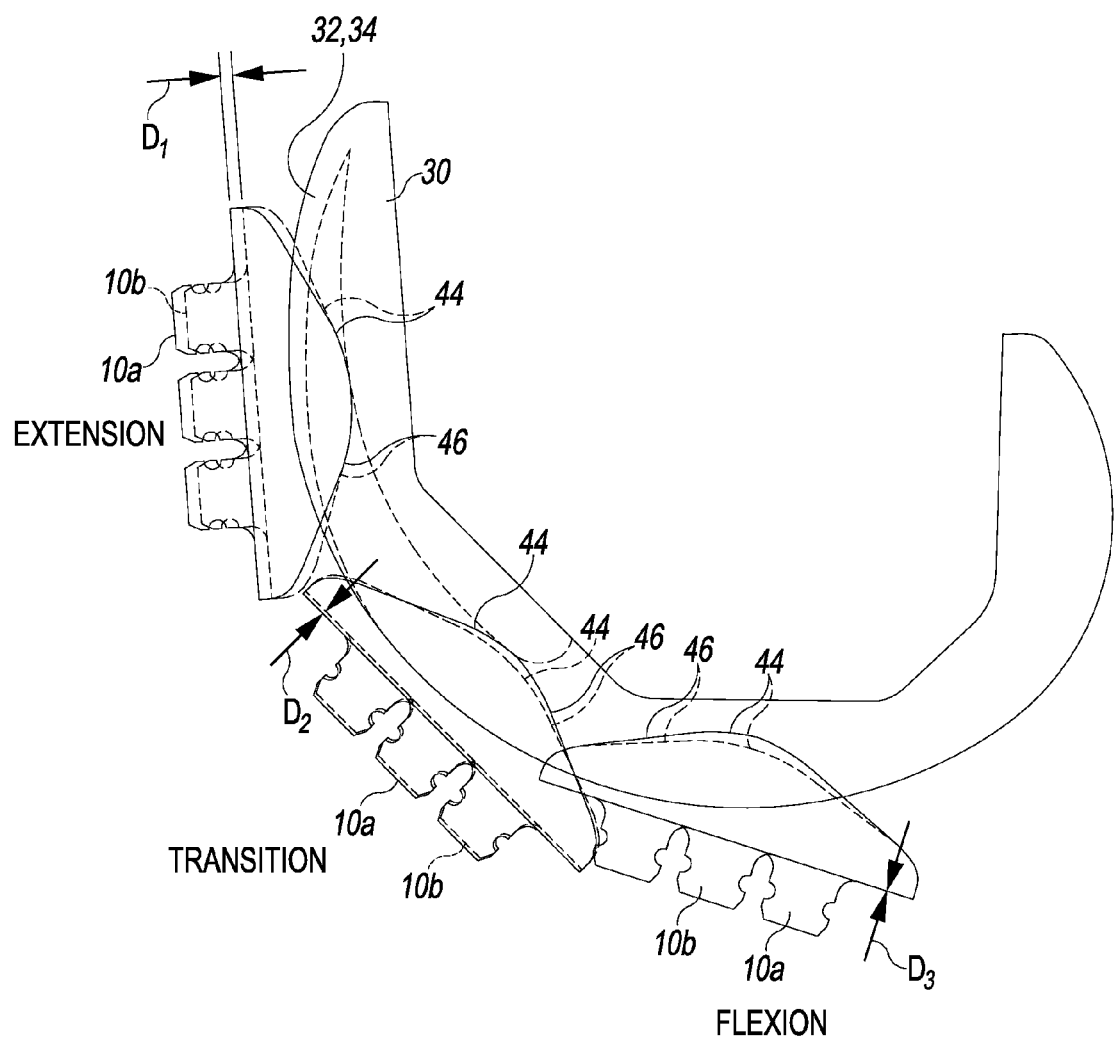
FIG. 9 is a diagrammatic sagittal cross sectional view showing two dome patella components from the chart of FIG. 8 that have common widths and different peak diameters superimposed upon one another and positioned in contact with the femoral component of the knee prosthesis.

The use of such a modified patella component 10 is shown in the diagrammatic sagittal cross sectional view of FIG. 9. As can be seen in FIG. 9, in extension, it is the partial hemispherically-shaped peak surface 44 of the component's posterior bearing surface 20 that articulates with the femoral condyle surfaces 32, 34 of the femoral component 30. As such, use of a dome patella component 10a having a partial hemispherically-shaped peak surface 44 with a smaller diameter (i.e., a more pointed component) creates a tighter extension gap than use of a dome patella component 10b having a partial hemispherically-shaped peak surface 44a with a larger diameter (i.e., a flatter component). This is shown geometrically in FIG. 9 where it is shown that during extension the anterior surface 40 of the more pointed dome patella component 10a is spaced apart anteriorly from the anterior surface 40 of the flatter dome patella component 10b by a distance $D_1$. In this illustrative embodiment described herein the offset distance ($D_1$) is 0.90 mm.

As the knee moves from extension to flexion, the offset lessens to the point where the anterior surface 40 of the more pointed dome patella component 10a is congruent with the anterior surface 40 of the flatter dome patella component 10b. In particular, in flexion, it is the conically-shaped surface 46 of the component's posterior bearing surface 20 that articulates with the femoral condyle surfaces 32, 34 of the femoral component 30. Because the conically-shaped surfaces 46 of each of the commonly-sized components 10 are identical with one another, use of the more pointed dome patella component 10a creates the same flexion gap as use of the flatter dome patella component 10b. This is shown geometrically in FIG. 9 where it is shown that as the knee transitions from extension to flexion, the anterior offset of the anterior surface 40 of the more pointed dome patella component 10a from the anterior surface 40 of the flatter dome patella component 10b lessens (e.g., the distance $D_2$ between the two surfaces is 0.30 mm at a point in transition between extension and flexion).

Once the knee is in flexion, only the conically-shaped surface 46 of the component's posterior bearing surface 20 articulates with the femoral condyle surfaces 32, 34 of the femoral component 30 (i.e., the partial hemispherically-shaped peak surface 44 is no longer articulating with the femoral condyle surfaces 32, 34). As such, in flexion, the anterior offset of the anterior surface 40 of the more pointed dome patella component 10a from the anterior surface 40 of the flatter dome patella component 10b no longer exists and the two surfaces are congruent with one another (e.g., the distance $D_3$ between the two surfaces is 0.00 mm).

As can be seen from FIG. 9, by varying the diameter of the partial hemispherically-shaped peak surface 44, the extension gap may be altered independently of the flexion gap. As such, the surgeon may select between a number of commonly-sized dome patella components (e.g., a number of 41 mm components) to tighten or loosen the extension gap without altering the flexion gap.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. An implantable orthopaedic knee prosthesis assembly, comprising:
   a first dome patella component having (i) a posterior bearing surface configured to articulate with the femoral condyles of an implantable femoral component, and (ii) an anterior surface having a number of pegs extending outwardly therefrom, wherein, when viewed in a coronal cross sectional view, (a) the posterior bearing surface of the first dome patella component has a curved peak surface that includes a posterior-most point of the first dome patella component, and (b) a first imaginary line segment extends orthogonally from the anterior surface of the first dome patella component to the posterior-most point of the first dome patella component, and
   a second dome patella component having (i) a posterior bearing surface configured to articulate with the femoral condyles of an implantable femoral component, (ii) an anterior surface having a number of pegs extending outwardly therefrom, and (iii) a medial/lateral width that is the same as the medial/lateral width of the first dome patella component, wherein, when viewed in a coronal cross sectional view, (a) the posterior bearing surface of the second dome patella component has a curved peak surface that includes a posterior-most point of the second dome patella component, and (b) a second imaginary line segment extends orthogonally from the anterior surface of the second dome patella component to the posterior-most point of the second dome patella component, the second imaginary line segment being longer than the first imaginary line segment,
   wherein the curved peak surface of both the first and second dome patella components comprises a section of a sphere that is less than a hemisphere, and
   the posterior bearing surface of both the first and second dome patella components further has a conically-shaped surface that extends anteriorly away from the curved peak surface and transitions into a rounded edge surface that extends anteriorly away from the conically-shaped surface in the direction toward the anterior surface.

2. The implantable orthopaedic knee prosthesis assembly of claim 1, further comprising:
   a third dome patella component having (i) a posterior bearing surface configured to articulate with the femoral condyles of an implantable femoral component, (ii) an anterior surface having a number of pegs extending outwardly therefrom, and (iii) a medial/lateral width that is the same as the medial/lateral width of both the first dome patella component and the second dome patella component, wherein, when viewed in a coronal cross sectional view, (a) the posterior bearing surface of the third dome patella component has a curved peak surface that includes a posterior-most point of the third dome patella component, and (b) a third imaginary line segment extends orthogonally from the anterior surface of the third dome patella component to the posterior-most point of the third dome patella component, the third imaginary line segment being longer than both the first imaginary line segment and the second imaginary line segment.

3. The implantable orthopaedic knee prosthesis assembly of claim 1, wherein each of the first and second dome patella components comprises a monolithic polyethylene body.

4. The implantable orthopaedic knee prosthesis assembly of claim 1, wherein:
   the first dome patella component comprises a first number of pegs extending anteriorly away from the anterior surface of the first dome patella component,
   the second dome patella component comprises a second number of pegs extending anteriorly away from the anterior surface of the second dome patella component,
   the first number of pegs have the same diameter as the second number of pegs, and
   the first number of pegs are arranged in the same pattern on the anterior surface of the first dome patella component as the second number of pegs are arranged on the anterior surface of the second dome patella component.

* * * * *